United States Patent

Markkula et al.

[11] Patent Number: 6,063,395
[45] Date of Patent: May 16, 2000

[54] DRUG DELIVERY DEVICE ESPECIALLY FOR THE DELIVERY OF PROGESTINS AND ESTROGENS

[75] Inventors: Tommi Markkula; Juba Ala-Sorvari; Harri Jukarainen, all of Turku; Matti Lehtinen, Piispanristi; Jarkko Ruohonen, Vanhalinna, all of Finland

[73] Assignee: Leiras Oy, Turku, Finland

[21] Appl. No.: 09/190,606

[22] Filed: Nov. 12, 1998

[51] Int. Cl.[7] ...................................................... A61F 13/00
[52] U.S. Cl. .......................... 424/422; 424/473; 424/486; 424/449
[58] Field of Search .................................... 424/422, 424, 424/473, 449, 486

[56] References Cited

U.S. PATENT DOCUMENTS

| | | | |
|---|---|---|---|
| 3,854,480 | 12/1974 | Zaffaroni | 128/260 |
| 4,244,949 | 1/1981 | Gupta | 424/243 |
| 4,957,119 | 9/1990 | de Nijs | 128/832 |
| 5,088,505 | 2/1992 | de Nijs | 128/830 |
| 5,150,718 | 9/1992 | de Nijs | 128/832 |
| 5,733,569 | 3/1998 | Moo-Young et al. | 424/424 |
| 5,824,736 | 10/1998 | Kobayashi et al. | 514/588 |

FOREIGN PATENT DOCUMENTS 0 589 386  3/1994  European Pat. Off. .

OTHER PUBLICATIONS

Sun et al., "Effect of Polymer Composition...," 5 *J. Controlled Release* 69–78 (1987).
Ghannam et al., "Kinetics and Thermodynamics of Drug...," 12 *Drug Dev. Ind. Pharm.* 303–325 (1986).
Sun et al., "Kinetics and Thermodynamics of Drug...," 12 *Drug Dev. Ind. Pharm.* 327–348 (1986).

*Primary Examiner*—Thurman K. Page
*Assistant Examiner*—Amy Pulliam
*Attorney, Agent, or Firm*—James C. Lydon

[57] ABSTRACT

The invention relates to a delivery device for the controlled release of a therapeutically active agent, especially a progestin or an estrogen, over a prolonged period of time, said device including a core which contains the therapeutically active agent, and a membrane encasing the core wherein said membrane is made of an elastomer. According to the invention, the elastomer is a siloxane-based elastomer which includes 3,3,3-trifluoropropyl groups attached to the Si-atoms of the siloxane units.

12 Claims, 2 Drawing Sheets

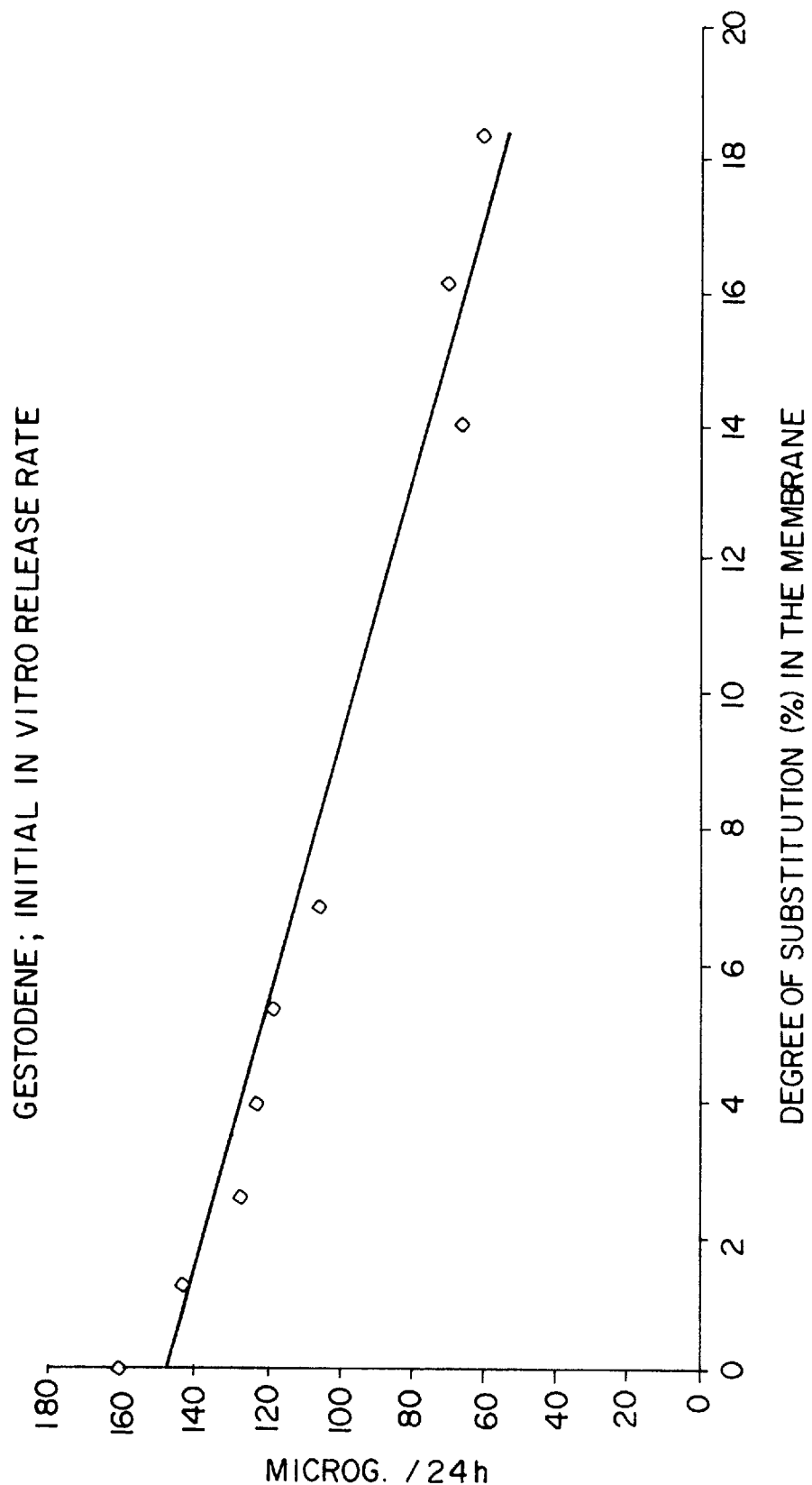

DRUG DELIVERY DEVICE ESPECIALLY FOR THE DELIVERY OF PROGESTINS AND ESTROGENS

FIELD OF THE INVENTION

This invention relates to a drug delivery device, particularly to an implantable device intended for subcutaneous administration of a drug at a substantially constant rate for a prolonged period of time.

BACKGROUND OF THE INVENTION

The publications and other materials used herein to illuminate the background of the invention, and in particular, cases to provide additional details respecting the practice, are incorporated by reference.

There is a great need for long-acting drug delivery devices, especially for contraceptives, which require a minimum of medical guidance. This concerns particularly the underdeveloped and developing countries where the medical infrastructure is weak and where family planning can be organized only to an insufficient level.

Contraceptive subcutaneous implants are known in the art. As example can be mentioned the commercially available product Norplant®, which is an implant having a core containing levonorgestrel as the active substance, and where the core it surrounded by a membrane of a silicone elastomer of poly(dimethylsiloxane) (PDMS). A special preparation of this kind is Jadelle® in which the core is a poly (dimethylsiloxane) based matrix with levonorgestrel dispersed therein. The membrane is an elastomer made from PDMS and silica filler, which, besides giving necessary strength properties to the membrane, also retards the permeation of the active agent through the membrane. U.S. Pat. No. 3,854,480 describes a drug delivery device, e.g. an implant, for releasing a drug at a controlled rate for a prolonged period of time. The device has a core of a matrix in which the drug is dispersed. The core is surrounded by a membrane that is insoluble in body fluids. The core matrix as well as the membrane are permeable to the drug by diffusion. The materials of the core and the membrane are chosen so that the drug diffuses through the membrane at a lesser rate than through the core matrix. Thus, the membrane controls the release rate of the drug. As a suitable polymer for the core matrix is mentioned poly(dimethylsiloxane) (PDMS), and as suitable polymers for the membrane are mentioned polyethylene and a copolymer of ethylene and vinyl acetate (EVA).

EP-B1-300306 describes an implant for subcutaneous or local use and for the release of a contraceptive agent for a relatively long time. The contraceptively active substance is dispersed in a core matrix and the core is surrounded by a membrane. As active substances are mentioned highly active progestins such as 3-keto-desogestrel, levonorgestrel and gestodene. The materials of the core matrix and the membrane are both based an copolymers of ethylene and vinyl acetate. The vinyl acetate concentration of the matrix polymer is higher than that of the membrane polymer. Therefore, the drug permeation of the membrane is slower than its permeation of the core matrix.

Devices manufactured from EVA suffer, however, from certain drawbacks. The materials are rather stiff and non-flexible and are therefore rather unconvenient to wear as implants beneath the skin.

Polysiloxanes, such as PDMS, are therefore preferred polymers in drug delivery devices for a great variety of different drugs. These polymers are particularly useful in subcutaneous implants, intrauterine devices and vaginal rings.

In EP-B1-300306, Example 1, it is mentioned that a polysiloxane layer around the implant did not retard the release rate of the drug. The retarding effect on the drug permeation that can be achieved by mixing silica into the PDMS is, however, rather limited. If silica is mixed into the PDMS polymer to about 40 weight-% of the final elastomer composition, typically a decrease in drug penetration rate of approximately 20% is achieved. In general, silica loading will have only a minimal influence on the drug permeation. The only way to achieve an essentially stronger retardation would be to use a thicker membrane. This would, however, result in devices of greater cross section and this would in turn lead to devices, such as implants and the like, which are difficult to insert or inject and unconvenient to wear.

The cross section of a cylindrical implant should not exceed 3 mm. Preferably, it should be in the range of 1.5 to 2.7 mm. This feature makes demands upon the maximal membrane thickness: the thickness should not be greater than 0.4 mm. The suitable length of the implant should not exceed 50 mm.

OBJECTS AND SUMMARY OF THE INVENTION

The object of this invention is to provide a drug delivery device, particularly an implantable device intended for subcutaneous administration of a drug at a substantially constant rate for a prolonged period of time.

The object is particularly to provide a device with which the drug release rate easily can be adjusted to a desirable level.

The object is particularly to provide a flexible and smooth device, which has a small cross section and which is easy to insert or inject and convenient to wear.

Thus, this invention concerns a delivery device for the controlled release of a therapeutically active agent over a prolonged period of time, said device comprising a core comprising said therapeutically active agent, and a membrane encasing said core wherein said membrane is made of an elastomer. According to the invention, the elastomer is a siloxane-based elastomer comprising 3,3,3-trifluoropropyl groups attached to the Si-atoms of the siloxane units.

BRIEF DESCRIPTION OF THE DRAWINGS

FIG. 2 shows the initial release rate in vitro of gestodene from a series of implants, where the release rate is plotted versus 3,3,3-trifluoropropyl substitution degree.

DETAILED DESCRIPTION OF THE INVENTION

The Elastomer

Figure 1:
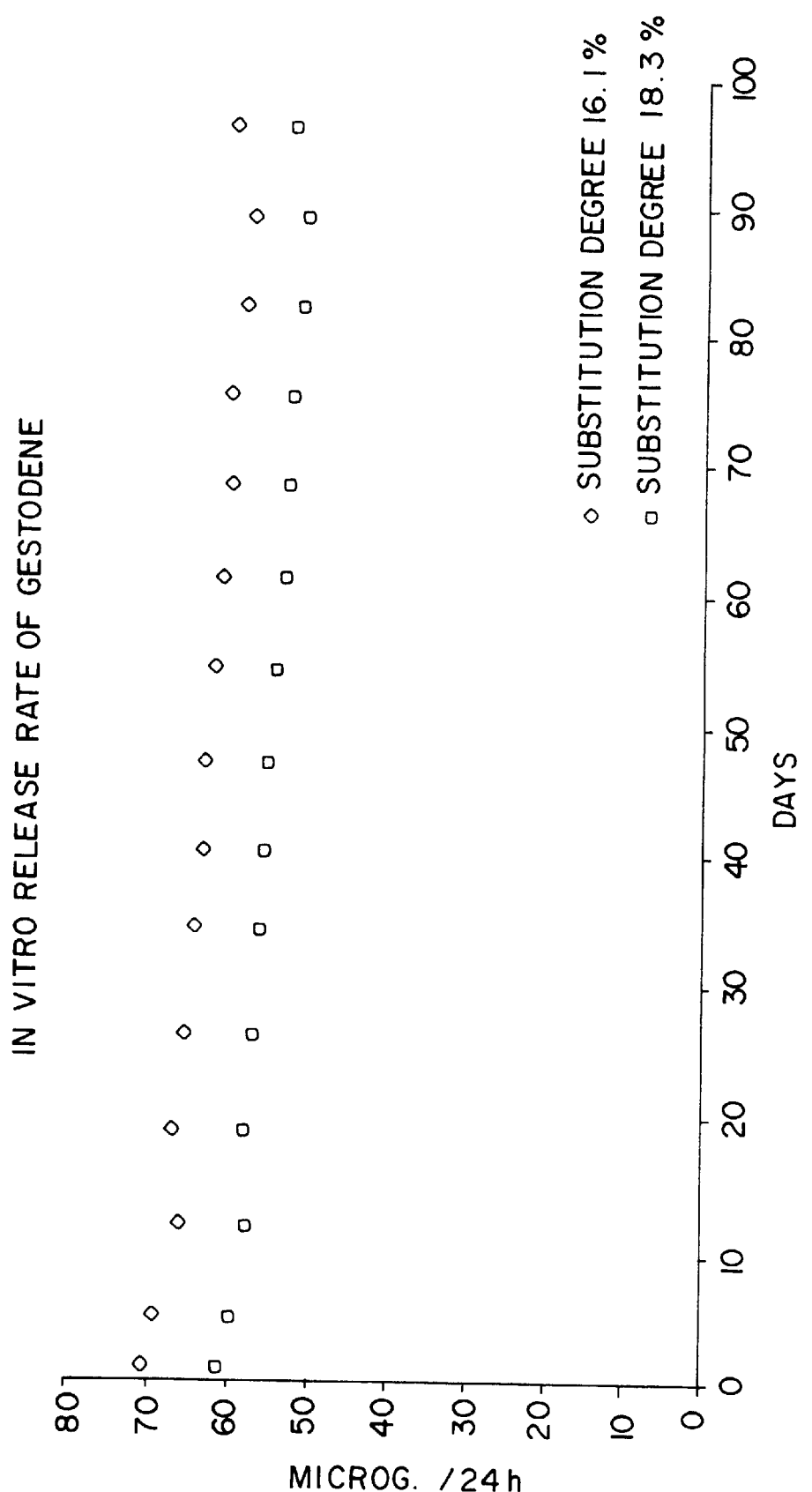
FIG. 1 shows the daily in vitro release rate of gestodene from two implants in which the membrane contains different amounts of 3,3,3-trifluoropropyl substituents.

The new elastomer suitable for use in the device according to this invention, particularly for use in the membrane of the device, is a siloxane-based elastomer comprising 3,3,3-trifluoropropyl groups attached to the Si-atoms of the siloxane units.

The term "siloxane-based elastomer" shall be understood to cover elastomers made of poly(disubstituted siloxanes) where the substituents mainly are lower alkyl, preferably alkyl groups of 1 to 6 carbon atoms, or phenyl groups, wherein said alkyl or phenyl can be substituted or unsubstituted. A widely used and preferred polymer of this kind is poly(dimethylsiloxane) (PDMS).

A certain amount of the substituents attached to the Si-atoms of the siloxane units in the elastomer shall be 3,3,3,-trifluoropropyl groups. Such an elastomer can be achieved in different ways. According to one embodiment, the elastomer can be based on one single crosslinked siloxane-based polymer, such as a poly(dialkyl siloxane) where a certain amount of the alkyl groups at the Si-atoms are replaced by 3,3,3-trifluoropropyl groups. A preferred example of such polymers is poly(3,3,3-trifluoropropyl methyl siloxane) the structure of which is shown as compound I below.

Compound I

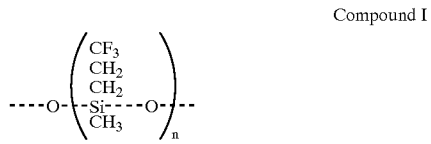

A polymer of this kind, in which approximately 50% of the methyl substituents at the Si-atoms replaced by 3,3,3-trifluoropropyl groups, is commercially available. The term "approximately 50%" means that the degree of 3,3,3-trifluoropropyl substitution is in fact somewhat below 50%, because the polymer must contain a certain amount (about 0.15% of the substituents) of crosslinkable groups such as vinyl or vinyl-terminated groups. Similar polymers having lower substitution degree of 3,3,3-trifluoropropyl groups can easily be synthetized.

The retarding effect of the 3,3,3-trifluoropropyl groups on the permeation of drugs across a membrane of the elastomer is dependent on the amount of these groups. Furthermore, the effect is highly dependent on the drug used. If the elastomer is made of one single polymer only, it would be necessary to prepare and use polymers with different amounts of 3,3,3,-trifluoropropyl groups for different drugs.

According to another embodiment, which is particularly preferred if suitable elastomers for several different drugs are needed, is to crosslink a mixture comprising a) a non-fluorosubstituted siloxane-based polymer and b) a fluorosubstituted siloxane-based polymer, where said polymer comprises 3,3,3,-trifluoropropyl groups attached to the Si-atoms of the siloxane units. The first ingredient of the mixture, the non-fluorosubstituted polymer, can be any poly(disubstituted siloxane) where the substituents mainly are lower alkyl, preferably alkyl groups of 1 to 6 carbon atoms, or phenyl groups, wherein said alkyl or phenyl can be substituted or unsubstituted. A preferred non-fluorosubstituted polymer is PDMS. The second ingredient of the mixture, the fluoro-substituted polymer, can for example be a poly(dialkyl siloxane) where a certain amount of the alkyl groups at the Si-atoms are replaced by 3,3,3-trifluoropropyl groups. A preferred example of such polymers is poly(3,3,3-trifluoropropyl methyl siloxane) as mentioned above. A particularly preferable polymer of this kind is a polymer having as high amount of 3,3,3,-trifluoropropyl substituents as possible, such as the commercially available polymer, in which approximately 50% of the methyl substituents at the Si-atoms are replaced by 3,3,3-trifluoropropyl groups. An elastomer with great permeation retarding effect can be achieved by using exclusively or mainly the aforementioned polymer. Elastomers with less retarding influence on the permeation of the drug can be obtained by using mixtures with increasing amounts of the non-fluorosubstituted siloxane-based polymer.

The elastomer should preferably comprise a filler, such as amorphous silica, in order to give a sufficient strength for the membrane made from said elastomer.

Methods for the Preparation of the Elastomer

According to one embodiment, the novel elastomer is prepared by crosslinking, in the presence of a catalyst, a vinyl-functional polysiloxane component and a silicon hydride-functional crosslinking agent.

By crosslinking is meant the addition reaction of the silicon hydride-functional crosslinking agent with the carbon-carbon double bond of the vinyl-functional polysiloxane component.

According to another embodiment, the elastomer is prepared by crosslinking the polymer in the presence of a peroxide catalyst.

The term "vinyl-functional" polysiloxane shall be understood to cover polysiloxanes substituted with vinyl groups or with vinyl-terminated groups. The "vinyl-functional polysiloxane component" and the "polysiloxane component" to be crosslinked shall also be understood to cover copolymers with polysiloxanes having vinyl substituents or vinylterminated substituents. For crosslinking, the amounts of the components are preferably selected so that the ratio of the molar amounts of the silicon hydrides to the double bonds is at least 1.

As stated above, the new elastomer can be made by crosslinking one single fluorosubstituted siloxane-based polymer, or by crosslinking a mixture of a non-fluorosubstituted siloxane-based polymer and a fluorosubstituted siloxane-based polymer. The term "vinyl-functional polysiloxane component" can thus be a mixture comprising a non-fluorosubstituted siloxane-based polymer and a fluorosubstituted siloxane-based polymer, where said polymer comprises 3,3,3,-trifluoropropyl groups attached to the Si-atoms of the siloxane units. Alternatively, the "vinyl-functional polysiloxane component" can be a single fluorosubstituted siloxane-based polymer, where said polymer comprises 3,3,3,-trifluoropropyl groups attached to the Si-atoms of the siloxane units.

The silicon hydride-functional crosslinking agent is preferably a hydride-functional polysiloxane which may be straight-chain, branched or cyclic.

The fluorosubstituted siloxane-based polymer is preferably a PDMS polymer where approximately 50% of the methyl groups in said PDMS have been replaced by 3,3,3,-trifluoropropyl groups.

A filler, such as amorphous silica, is preferably added to the vinyl-functional component before the crosslinking.

In case the elastomer is made by crosslinking a polymer component in the presence of a peroxide catalyst, such a polymer component can be a mixture comprising a non-fluorosubstituted siloxane-based polymer and a fluorosubstituted siloxane-based polymer comprising 3,3,3,-trifluoropropyl groups attached to the Si-atoms of the siloxane units. Alternatively, this polymer component can be a single fluorosubstituted siloxane-based polymer, where said polymer comprises 3,3,3,-trifluoropropyl groups attached to the Si-atoms of the siloxane units.

The catalyst to be used in the crosslinking is preferably a noble metal catalyst, most commonly a platinum complex in alcohol, xylene, divinyl siloxane or cyclic vinyl siloxane. An especially suitable catalyst is a Pt(0)-divinyl-tetramethyl disiloxane complex.

Different Types of Devices

The device can be any device suitable for delivery of an active agent at a controlled rate over a prolonged period of time. Thus, the device can take a wide variety of shapes and forms for administering the active agent at controlled rates to different areas of the body. Thus, the invention includes external and internal drug delivery devices such as transdermal patches, implants for releasing a therapeutically active agent in the body tissues, intravaginal rings and intrauterine devices.

According to a preferred embodiment, the device is an implant for subcutaneous use.

Construction of the Core

The core of the device can consist of the active agent as such, e.g. in liquid or crystallized form, or in a mixture with pharmaceutically acceptable excipients.

Preferably, the core is an elastomer matrix, such as a PDMS elastomer matrix in which the drug is dispersed.

According to an other alternative, the core matrix can be made of the novel elastomer, which is a siloxane-based elastomer comprising 3,3,3-trifluoropropyl groups attached to the Si-atoms of the siloxane units.

Therapeutically Active Agents

The therapeutically active agent is preferably a hormone, but is not restricted hereto. Especially preferable hormones are progestins, such as gestodene or levonorgestrel, and estrogens, and their derivatives such as esters.

Most preferably, the device is an implant for subcutaneous use and administration of progestins at a controlled rate over a prolonged period of time.

Manufacture of Implants

The implants according to this invention can be manufactured in accordance with standard techniques. The therapeutically active agent is mixed with the core matrix polymer such as PDMS, processed to the desired shape by molding, casting, extrusion, or other appropriate methods. The membrane layer can be applied onto the core according to known methods such as by mechanical stretching, swelling or dipping. Reference is made to the U.S.-patents U.S. Pat. Nos. 3,832,252, 3,854,480 and 4,957,119. An especially suitable method for preparation of the implants is disclosed in the Finnish patent FI 97947. This patent discloses an extrusion technology where prefabricated rods containing the active ingredient are coated by an outer membrane. Each such rod is, for example, followed by another rod without any active ingredient. The formed string is cut at the rods that contain no active agent. In this way, no special sealing of the ends of the implant is necessary.

The invention is described in more detail by the following non-limiting examples.

EXPERIMENTAL SECTION

The invention is described below in greater detail in the following examples.

Elatomers of different types (A–E) were prepared. Type A represents an elastomer made from a mixture comprosing fluorosubstituted (3,3,3-trifluoropropyl substitution degree 49.5%) and non-fluorosubstituted siloxane-based polymers wherein the crosslinking was performed by peroxide catalyst. Three different mixtures with varying amounts of fluorosubstituted polymer were prepared (Example 1). The B type (Examples 2 and 3) represents and elastomer made from a single fluorosubstituted siloxane-based polymer wherein the crosslinking was performed by peroxide catalyst. Type C (Example 4) represents an elastomer made from a mixture comprising fluorosubstituted (3,3,3-trifluoropropyl substitution degree 30%) and non-fluorosubstituted siloxane-based polymers wherein the crosslinking was performed by peroxide catalyst. The D type (Example 5) represents and elastomer made from a single fluorosubstituted siloxane-based polymer wherein the crosslinking was performed by hydrosilylation. Type E (Example 6) represents an elastomer made from a mixture comprising fluorosubstituted (3,3,3-trifluoropropyl substitution degree 49.5%) and non-fluorosubstituted siloxane-based polymers wherein the crosslinking was performed by hydrosilylation.

EXAMPLE 1

Type A Elastomers with Varying Amounts Fluorosubstituted Polymers

A series of 50 [and further 25 and 75] parts by weight of silica-filled poly(trifluoropropylmethylsiloxane-co-vinylmethylsiloxane), 50 [and 75 and 25 respectively] parts by weight of silica-filled poly(dimethylsiloxane-co-vinylmethylsiloxane) and 1.2 parts by weight of dibentsoylperoxide-polydimethylsiloxane paste were mixed with a 2-roll mill. The mixture was cured at +115° C. for 5 minutes with a thermal press to give 0.4 mm thick membranes, which were post-cured at +150° C. for 2 hours.

EXAMPLE 2

Elastomer Type B 100 parts by weight of silica-filled poly(trifluoropropylmethylsiloxane-co-dimethylsiloxane-co-vinylmethylsiloxane) (content of trifluoropropylmethylsiloxane units 60 mol-%; i.e. degree of trifluoropropyl substitution groups is 30%) and 1.2 parts by weight of dibentsoylperoxide-polydimethylsiloxane paste were mixed with a 2-roll mill. The mixture was cured at +115° C. for 5 minutes with a thermal press to give 0.4 mm thick membranes, which were post-cured at +150° C. for 2 hours.

EXAMPLE 3

Elastomer Type B 100 parts by weight of silica-filled poly(trifluoropropylmethylsiloxane-co-dimethylsiloxane-co-vinylmethylsiloxane) (content of trifluoropropylmethylsiloxane units 99 mol-%; i.e. degree of trifluoropropyl substitution 49.5%) and 1.2 parts by weight of dibentsoylperoxide-polydimethylsiloxane paste were mixed with a 2-roll mill. The mixture was cured at +115° C. for 5 minutes with a thermal press to give 0.4 mm thick membranes, which were post-cured at +150° C. for 2 hours.

EXAMPLE 4

Elastomer Type C 50 ports by weight of the silica-filled fluoro-substituted polysiloxane in Example 2, 50 parts by weight of silica-filled poly(dimethylsiloxane-co-vinylmethylsiloxane) and 1.2 parts by weight of dibentsoylperoxide-polydimethylsiloxane paste were mixed with a 2-roll mill. The mixture was cured at +115° C. for 5 minutes with a thermal press to give 0.4 mm thick membranes, which were post-cured at +150° C. for 2 hours.

EXAMPLE 5

Elastomer Type D 100 parts by weight of silica-filled poly(trifluoropropylmethylsiloxane-co-vinylmethylsiloxane) (substitution degree of 3,3,3-trifluoropropyl groups=49.5%), 0.04 parts by weight of Pt(0)-divinyltetramethyl-siloxane complex, 0.05 parts by weight of 1-ethinyl-1-cyclohexanol and 1.0 parts by weight of silicon hydride crosslinking agent were mixed with a two-chamber mixer. The mixture was cured at +115° C. for 5 minutes with a thermal press to give 0.4 mm thick membranes.

EXAMPLE 6

Elastomer Type E 50 parts by weight of the silica-filled fluoro-substituted polysiloxane in Example 5, 50 parts by weight of silica-filled poly(dimethylsiloxane-co-vinylmethylsiloxane), 0.04 parts by weight of Pt(0)-divinyltetramethylsiloxane complex, 0.05 parts by weight of 1-ethinyl-1-cyclohexanol and 1.0 parts by weight of silicon hydride crosslinking agent were mixed with a two-chamber mixer. The mixture was cured at +115° C. for 5 minutes with a thermal press to give 0.4 mm thick membranes.

Membrane Permeation Studies

The permeation of different drugs through elastomers of types A, B and C described above were tested.

The test apparatus described in the publication Yie W. Chien, Transdermal Controlled Systemic Medications, Marcel Dekker inc. New York and Basel 1987, page 173, was used in the permeation tests.

The drug fluxes (permeations) through membranes were measured with a two-compartment diffusion call at 37° C. (side-by-side diffusion cell, Crown Glass Company). The apparatus consisted of two concentric cells (donor and receptor compartments) that were separated by the elastomer membrane to be investigated. The donor and receptor compartments were both jacketed and thermostated by an external circulating bath and each compartment had a magnetic stirrer. A drug solution and solvent (without drug) was added into the donor and the receptor compartments. At each predetermined time interval, samples were withdrawn from the receptor compartment and replaced with the same volume of solvent. The amount of the drug that permeated through the membrane was measured by HPLC. In all measurements, the thickness (0.4 mm) of the membrane and the surface area of the membranes were constant.

In the following tables, the relative permeation through different elastomers were studied for different drugs. The reference elastomer is dimethylsiloxane-vinylmethylsiloxane copolymer, which contains silica filler. In the tables below, the term "trifluoropropyl substitution degree, %" has the same meaning as mentioned before and this percentage means the substituents at the Si-atoms of the siloxane units in the elastomer, i.e. the 3,3,3-trifluoropropyl substituents.

Drug 1: Gestodene

| Elastomer type | trifluoropropyl substitution degree, % | Relative permeation |
|---|---|---|
| reference | 0 | 1 |
| A | 7 | 0.63 |
| A | 16 | 0.37 |
| A | 29.5 | 0.18 |
| B | 30 | 0.45 |
| B | 49.5 | 0.06 |

Drug 2: 17-β-estradiol

| Elastomer type | trifluoropropyl substitution degree, % | Relative permeation |
|---|---|---|
| reference | 0 | 1 |
| B | 30 | 0.23 |
| B | 49.5 | 0.04 |

Drug 3: Nestorone™ (16-methylene-17-α-acetoxy-19-norprogesterone)

| Elastomer type | trifluoropropyl substitution degree, % | Relative permeation |
|---|---|---|
| reference | 0 | 1 |
| B | 49.5 | 0.29 |

Drug 4: Levonorgestrel

| Elastomer type | trifluoropropyl substitution degree, % | Relative permeation |
|---|---|---|
| reference | 0 | 1 |
| B | 20 | 0.77 |
| B | 30 | 0.41 |
| B | 49.5 | 0.05 |
| C | 11 | 0.73 |

An elastomer according to the invention is, for example, highly suited for controlling, in implants and in intrauterine and intravaginal devices, the permeation of drugs having hormonal action.

The elastomer according to the invention is particularly suitable for the release of hormonally active drugs such as progestins and estrogens.

Preparation of implants containing gestodene as the active agent

The implants manufactured consisted of three parts: a core containing gestodene in a polymer matrix, a membrane covering the core and silicone adhesive end-caps.

Membrane Preparation

The poly(trifluoropropylmethylsiloxane-co-vinylmethylsiloxane) used in the implant tests described in the following is a copolymer, where the content of 3,3,3-trifluoropropylmethyl siloxane units is nearly 100 mol-%, i.e. corresponding to a substitution degree of silicon of nearly 50%.

[0, 5, 10, 15, 20, 25, 45, 50] 55 parts (by weight) of silica-filled poly(trifluoropropylmethylsiloxane-covinylmethylsiloxane), [100, 95, 90, 85, 80, 75, 55, 50 respectively] 45 parts of silica-filled poly(dimethylsiloxane-co-vinylmethylsiloxane) and 1.2 parts of dibenzoylperoxide-poly(dimethylsiloxane) paste were mixed with a 2-roll mill. The mixture was extruded to a tube-like form with a wall thickness of 0.2 mm and cured by heat. The membrane was post-cured at +150° C. for 2 hours and cut to 50 mm pieces.

Core Preparation 50 parts of poly(dimethylsiloxane-co-vinylmethylsiloxane) which included dichlorobenzoylperoxide, and 50 parts of gestodene were mixed with a two-chamber mixer. The mixture was casted into a PTFE-coated stainless steel mold, which was heated at +150° C. for 30 minutes. The cores were removed, cooled and cut to 40 mm pieces.

Implant Preparation 50 mm membrane pieces were swelled with cyclohexane and the gestodene containing cores were inserted. Cyclohexane was allowed to evaporate and the ends of the implants were closed with a silicone adhesive. After 24 hours the ends were cut to give 2 mm end-caps.

Drug Release Tests

The release rate of the drug from the implant was measured in vitro as follows:

The implants were attached into a stainless steel holder in vertical position and the holders with the implants were placed into glass bottles containing 75 ml of a dissolution medium. The glass bottles were shaked in shaking waterbath 100 rpm at 37° C. The dissolution medium was withdrawn and replaced by a fresh dissolution medium at predetermined time intervals, and the released drug was analysed by HPLC. The concentration of the dissolution medium and the moment of change (withdrawal and replacement) of medium were selected so that sink-conditions were maintained during the test.

Results

FIG. 1 shows the daily in vitro release rate of gestodene from two implants in which the membrane contains different amounts of 3,3,3-trifluoropropyl substituents. The square marked curve refers to a membrane with a trifluoropropyl substitution degree of 18.3% (i.e. 18.3% of the substituents at the Si-atoms of the siloxane units in the membrane elastomer are 3,3,3-trifluoropropyl groups), and the diamond marked curve refers to a membrane with a trifluoropropyl substitution degree of 16.1% (as defined above). Thus, the experiments demonstrate clearly the retarding effect caused by the 3,3,3-trifluoropropyl substitution of the membrane polymer.

FIG. 2 shows the initial in vitro release rate of gestodene from a series of implants, where the release rate is plotted versus 3,3,3-trifluoropropyl substitution degree. This test shows clearly the retarding effect of the trifluoropropyl substitution on the drug release rate. There is almost a linear relationship between the release rate and the trifluoropropyl substitution degree of the membrane elastomer.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

What is claimed is:

1. A delivery device for the controlled release of a therapeutically active agent over a prolonged period of time, said device comprising a core comprising said therapeutically active agent, and a membrane encasing said core, wherein said membrane is made of an elastomer, characterized in that the elastomer is a siloxane-based elastomer comprising 3,3,3-trifluoropropyl groups attached to the Si-atoms of the siloxane units, wherein 1 to approximately 50% of the substituents attached to the Si-atoms in the siloxane units of the elastomer are 3,3,3-trifluoropropyl groups; and wherein the elastomer is made of either (i) a mixture comprising a) a non-fluorosubstituted siloxane-based polymer and b) a fluorosubstituted siloxane-based polymer, said polymer comprising 3,3,3-trifluoropropyl groups attached to the Si-atoms of the siloxane units; or (ii) a single siloxane-based polymer comprising 3,3,3-trifluoropropyl groups attached to the Si-atoms of the siloxane units, wherein said polymer or mixture of polymers are crosslinked to form the elastomer.

2. The device according to claim 1, characterized in that it is an implantable device intended for subcutaneous administration of the active agent.

3. The device according to claim 1, characterized in that the mixture of polymers is a mixture of a) poly(dimethylsiloxane) and b) poly(dimethylsiloxane) in which the methyl groups attached to the Si-atoms of the siloxane units to some extent have been replaced by 3,3,3,-trifluoropropyl groups.

4. The device according to claim 3, characterized in that approximately 50% of the methyl groups in the polymer b) have been replaced by 3,3,3,-trifluoropropyl groups.

5. The device according to claim 1, characterized in that the the core is an elastomer matrix in which the drug is dispersed.

6. The device according to claim 5, characterized in that the core elastomer is PDMS.

7. The device according to claim 5, characterized in that also the core elastomer is a siloxane-based elastomer comprising 3,3,3-trifluoropropyl groups attached to the Si-atoms of the siloxane units.

8. The device according to claim 1, characterized in that the therapeutically active agent is a hormone.

9. The device according to claim 8, characterized in that the hormone is a progestin or an estrogen.

10. The device according to claim 9, characterized in that the progestin is gestodene.

11. The device according to claim 10, characterized in that the device is an implant for subcutaneous use.

12. The device according to claim 1, characterized in that the elastomer comprises a filler.

* * * * *

UNITED STATES PATENT AND TRADEMARK OFFICE
CERTIFICATE OF CORRECTION

PATENT NO. : 6,063,395
DATED : May 16, 2000
INVENTOR(S) : Tommi Markkula, Juha Ala-Sorvari, Harri Jukarainen, Matti Lehtinen and Jarkko Ruohonen It is certified that error appears in the above-indentified patent and that said Letters Patent is hereby corrected as shown below:

On the cover page, the name of the second inventor should appear as follows: Juha Ala-Sorvari Signed and Sealed this Sixth Day of March, 2001

Attest:

NICHOLAS P. GODICI

Attesting Officer

Acting Director of the United States Patent and Trademark Office